United States Patent [19]

Peterson

[11] 4,372,877

[45] Feb. 8, 1983

[54] DI(ACYLPEROXY)-1,4-CYCLOHEXANE DIMETHANOL-BIS-CARBONATES

[75] Inventor: David Peterson, Hercules, Calif.

[73] Assignee: U.S. Peroxygen Company, Richmond, Calif.

[21] Appl. No.: 318,308

[22] Filed: Nov. 5, 1981

[51] Int. Cl.$^3$ .................................... C07C 179/14
[52] U.S. Cl. ........................ 260/453 RZ; 260/463
[58] Field of Search ................... 260/453 RZ, 463

[56] References Cited

U.S. PATENT DOCUMENTS

| | | | |
|---|---|---|---|
| 3,499,919 | 3/1970 | Gerritsen et al. | 260/453 |
| 3,528,956 | 9/1970 | Gerritsen et al. | 260/92.8 |
| 3,720,700 | 3/1973 | Norback | 260/463 |
| 3,855,351 | 12/1974 | Sanchez | 260/861 |
| 3,857,828 | 12/1974 | Sanchez | 260/92.8 |
| 4,129,613 | 12/1978 | Lewis et al. | 260/861 |
| 4,137,252 | 1/1979 | Komai et al. | 260/463 |
| 4,285,877 | 8/1981 | Halle et al. | 260/453 |

Primary Examiner—John M. Ford
Assistant Examiner—Robert C. Whittenbaugh
Attorney, Agent, or Firm—Townsend and Townsend

[57] ABSTRACT

Di(acylperoxy)-bis-carbonates of the formula:

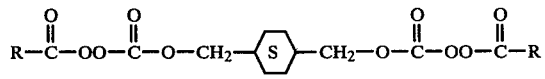

wherein each R is selected from alkyl and aryl of up to about 20 carbon atoms. The new molecules have exceptional thermal stability, which facilitates storage at ambient temperatures. They have utility in initiating the polymerization of ethylenically unsaturated monomers and for curing polymers such as unsaturated polyester resins.

5 Claims, No Drawings

DI(ACYLPEROXY)-1,4-CYCLOHEXANE DIMETHANOL-BIS-CARBONATES

BACKGROUND OF THE INVENTION

1. Field of the Invention

This invention relates to organic peroxide polymerization initiators and to their use in the polymerization of monomers and in the curing of resins such as unsaturated polyesters. In particular, the invention relates to peroxy dicarbonates having a cyclohexyl ring disubstituted in its 1,4 positions with acylperoxy carbonate groups.

2. Brief Description of the Prior Art

U.S. Pat. Nos. 3,499,919 and 3,528,956 disclose dicyclohexyl peroxy dicarbonates substituted at the 4 positions of the cyclohexyl rings by alkyl, cyclohexyl or cyclohexylalkyl and their use as polymerization catalysts.

U.S. Pat. Nos. 3,855,351 and 3,857,828 teach the use of di(2-phenoxyethyl) peroxy dicarbonate as a polymerization initiator and as a catalyst for curing polyester resins.

U.S. Pat. No. 4,129,613 teaches certain acylperoxy carbonic esters, in which the alkyl groups of the acyl portion and of the ester moiety together contain a total of 17 to about 25 carbon atoms, and their use in curing polyester resins.

U.S. Pat. No. 3,720,700 discloses the chemical compound di-cetyl peroxy dicarbonate, its method of production and its use as an initiator in the polymerization of unsaturated compounds such as vinyl chloride.

U.S. Pat. No. 4,137,252 discloses dicyclododecyl peroxy dicarbonate as an improved initiator having a stability that permits storage at room temperature.

U.S. Pat. No. 4,285,877 discloses di(2-methyl-2-phenyl propyl) peroxy dicarbonate and other novel (2-alkyl-2-phenyl) substituted peroxy dicarbonates. The molecules are used for initiating the polymerization of molecules having ethylenic unsaturation such as vinyl chloride and for curing unsaturated polyester resins. They are disclosed as being room temperature solids and having ambient temperature stability.

SUMMARY OF THE INVENTION

The present invention provides novel di(acylperoxy)-bis-carbonates of the formula:

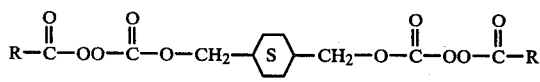

wherein each R is selected from alkyl and aryl of up to about 20 carbon atoms. In the preferred embodiment each R is selected from phenyl or alkyl of up to about 12 carbon atoms. The alkyl group may be branched or straight chain. The aryl group, preferably phenyl, may contain ring substituents such as alkyl, halo or alkoxy.

The new molecules may be used for curing polyester resins by subjecting ethylenically unsaturated polyester resins and crosslinkable monomer to crosslinking conditions in the presence of a crosslinking initiating amount of the novel compound. Similarly, the new molecules may be used for initiating the polymerization of ethylenically unsaturated monomers by subjecting the monomer to polymerization conditions in the presence of a polymerizing amount of the new compounds.

The bis-carbonates of the present invention may be prepared by reacting a corresponding peracid having the desired R group with a corresponding haloformate, particularly a chloroformate in the presence of a base, in accordance with the following equation:

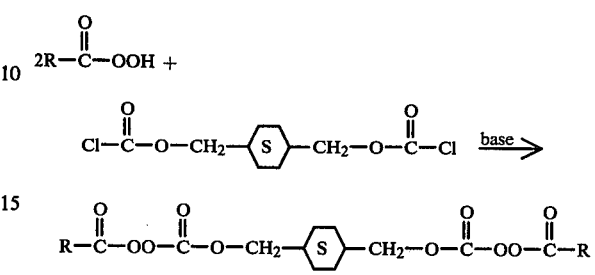

wherein each R is selected from alkyl and aryl of up to about 20 carbon atoms.

The following examples will illustrate the synthesis of the bis-carbonates of the present invention and their utility as polymerization initiators.

EXAMPLE 1 di(acetylperoxy)-1,4-cyclohexane dimethanol bis-carbonate (APCD)

To 200 ml of CH$_2$Cl$_2$ at 5° C. was added 92.85 g of 35% peracetic acid (0.427 mole, 2.3 eq) in acetic acid and 50.00 g of 1,4-cyclohexane dimethanol bis-chloroformate (0.186 mole, 1.0 eq). Then 70.00 g of pyridine (0.885 mole, 4.76 eq) was added over 1½ hours at 5°–10° C. The mixture was stirred at 10° C. for another hour and then partitioned with the addition of 150 ml of ether and 150 ml of saturated NaCl solution. The organic layer was washed with 3×200 ml of 2% HCl solution, 2×200 ml of saturated NaHCO$_3$ solution, dried over MgSO$_4$ and evaporated to leave a gummy solid. The solid was mixed with 10 ml of CH$_2$Cl$_2$ and then precipitated by adding 40 ml of MeOH. The solid was collected by filtration and dried to give the product weighing 26.67 g. The M.P. was 85°–86° C. and the A.O. purity was 97.4%.

EXAMPLE 2 di(lauroylperoxy)-1,4-cyclohexane dimethanol bis-carbonate (LPCD)

To 72.96 g of 92.5% perlauric acid (0.312 mole, 2.1 eq) and 300 ml of ether at 5° C. was added 27.04 g of pyridine (0.342 mole, 2.3 eq). Then 40.0 g of 1,4-cyclohexanedimethanol bis-chloroformate (0.149 mole, 1.0 eq) was added over 1 hour at 5°–10° C. The mixture was stirred for another hour at 5° C. and then partitioned with the addition of 100 ml of cold ether and 80 ml of cold 2% HCl solution. The organic layer was washed with 2×80 ml of 2% HCl solution, 2×80 ml of 3% NaOH solution, 80 ml of saturated NaHCO$_3$ solution, and then dried over MgSO$_4$, and evaporated to leave a sticky solid. The solid was stirred with 100 ml of pet ether and then filtered to give the product weighing 28.66 g. The M.P. was 60°–62° C. and the A.O. purity was 87.8%.

EXAMPLE 3 di(benzoylperoxy)-1,4-cyclohexanedimethanol bis-carbonate (BPCD)

To 11.62 g of 86.6% perbenzoic acid (0.073 mole, 2.1 eq) and 80 ml of ether at 5° C. was added 9.34 g of 1,4-cyclohexanedimethanol bis-chloroformate (0.035 mole, 1.0 eq). Then 6.31 g of pyridine (0.080 mole, 2.3 eq) was added over 30 minutes at 5° C. The mixture was stirred at 5° C. for another 30 minutes and then partitioned with the addition of 100 ml of cold ether and 70 ml of cold 2% HCl solution. The organic layer was washed with 70 ml of cold 2% HCl solution, 2×70 ml of cold 3% NaOH solution, 70 ml of cold H₂O, and then dried over MgSO₄ and evaporated to leave a sticky solid. The solid was stirred with 100 ml of cold ether and dried under vacuum to leave the product weighing 3.33 g. The M.P. was 95°–100° C. and the A.O. purity was 89.8%.

Table I provides the ten-hour half-life of the compounds of the instant invention synthesized in Examples 1–3. Prior art peroxides 4 and 5 are shown in Table I for comparison.

TABLE I

| | Peroxide | Ten-Hour Half-Life Temperature, °C. (0.1 M in benzene) |
|---|---|---|
| 1. | APCD | 55.2 |
| 2. | LPCD | 51.4 |
| 3. | BPCD | 52.3 |
| 4. | Phenoxyethyl peroxydicarbonate | 42.2 |
| 5. | Di(4-t-butylcyclohexyl) peroxydicarbonate | 43.0 |

Table II illustrates the outstanding storage stability of the new molecules. APCD from Example 1 is selected as representative and was tested over a period of 89 days at 40° C. Representative peroxy carbonate and dicarbonates of the prior art are also included for comparison.

TABLE II

Storage Stability at 40° C.

| Peroxide Days Elapsed | APCD 9.19 | | di(phenoxyethyl) peroxydicarbonate 4.42 | | di(4-t-butylcyclohexyl) peroxydicarbonate 4.01 | | acetyl peroxystearyl carbonate 4.29 | |
|---|---|---|---|---|---|---|---|---|
| | A.O. | % Purity | A.O. | % Purity | A.O. | % Purity | A.O. | % Purity |
| 0 | 9.15 | 99.6 | 4.31 | 97.4 | 3.92 | 97.8 | 4.04 | 94.1 |
| 7 | 9.14 | 99.5 | 4.17 | 94.4 | 3.86 | 96.4 | 4.01 | 93.5 |
| 14 | 9.03 | 98.3 | 4.12 | 93.3 | 3.86 | 96.4 | 4.00 | 93.1 |
| 28 | 8.98 | 97.7 | 4.03 | 91.1 | 3.82 | 95.2 | 3.92 | 91.5 |
| 59 | 8.77 | 95.4 | 3.74 | 84.7 | 3.73 | 93.0 | 3.77 | 87.9 |
| 89 | 8.58 | 93.4 | 3.23 | 73.1 | 3.74 | 93.2 | 3.38 | 78.8 |

As mentioned, the instant bis-carbonates are useful for the initiation of monomers having polymerizable ethylenic or vinyl unsaturation, such as ethylene, styrene, methyl methacrylate and vinyl chloride and copolymers thereof. Tables III and IV illustrate such utility with vinyl chloride monomer. The data was generated with suspension polymerization performed in 12 ounce pop bottles using uninhibited monomer. Duplicate bottles were analyzed at each time interval for which data is listed. Bottles were frozen before venting off of excess monomer. Mixing speed of the pop bottles was 42 rpm. The water to vinyl chloride monomer ratio was 2.50. Each pop bottle contained 0.35 gms Dow Methocel 90 HG, 100 cps suspension agent per 100 gms vinyl chloride monomer.

TABLE III

Vinyl Chloride polymerization at 55° C.

| Peroxide | % wt | Moles ($\times 10^{-4}$)/ 100g VCM | % Conversion 1.5 Hrs. | 3.5 Hrs. | 5.5 Hrs. |
|---|---|---|---|---|---|
| 1. APCD | 0.030 | 0.85 | — | — | 35.7 |
| | 0.040 | 1.15 | — | — | 45.6 |
| | 0.051 | 1.45 | — | — | 55.7 |
| | 0.060 | 1.72 | — | — | 60.5 |
| | 0.070 | 2.01 | — | — | 71.5 |
| | 0.080 | 2.30 | — | — | 83.0 |
| | 0.0775 | 2.23 | 13.6 | 42.0 | 80.3 |
| 2. LPCD | 0.126 | 2.01 | — | — | 60.9 |
| | 0.145 | 2.30 | — | — | 72.0 |
| 3. BPCD | 0.081 | 1.72 | — | — | 55.7 |
| | 0.095 | 2.01 | — | — | 62.1 |
| | 0.109 | 2.30 | — | — | 73.6 |

TABLE IV

Vinyl Chloride polymerization at 60° C.

| Peroxide | % wt | Moles ($\times 10^{-4}$)/ 100g VCM | % Conversion 1.5 Hrs. | 3.5 Hrs. | 5.0 Hrs. |
|---|---|---|---|---|---|
| 1. APCD | 0.030 | 0.85 | — | — | 48.5 |
| | 0.040 | 1.15 | — | — | 65.9 |
| | 0.051 | 1.45 | — | — | 86.6 |
| | 0.0475 | 1.36 | 15.1 | 46.9 | 83.1 |
| 2. LPCD | 0.072 | 1.15 | — | — | 51.4 |
| | 0.091 | 1.45 | — | — | 65.4 |
| 3. BPCD | 0.040 | 0.85 | — | — | 43.4 |
| | 0.054 | 1.15 | — | — | 58.6 |
| | 0.066 | 1.40 | — | — | 72.4 |

Aside from the selection of the di(acylperoxy)-bis-carbonates having the structure discussed above, the practice of the present methods of polymerization involving a monomer mass containing one or more monomers, such as ethylene, styrene, methyl methacrylate and vinyl chloride, is consistent with prior art procedures for initiating the polymerization of such monomers. Thus, the present di(acylperoxy)-bis-carbonates are added in effective amounts, generally comparable to amounts of those initiators previously used, and usually within the range of about 0.005% to 3% by weight of the monomer content and more commonly about 0.01–0.5% by weight of the monomer content. For practical purposes the minimum amount of the di(acylperoxy)-bis-carbonates is added which will effectively initiate the polymerization of the monomer mass within the desired period of time. The usual conditions of temperature, pressure, solvents, and the like used in the polymerization of these monomers may be employed. In addition, it is contemplated that co-catalysts may be included to initiate the polymerization.

As mentioned above, the new molecules can be used for curing of polyester resins and this utility is illustrated in Tables V and VI below. Typical prior art peroxy dicarbonates and carbonates of the prior art are included for comparison.

TABLE V

Hot Block Gel Tests With Polyester Resin
Resin: MR 941 (U.S.S. Chemical - orthophthalic)
Block Temperature: 180° F.
Concentrations of peroxide adjusted to 100% purity basis, 1% wt

| | Peroxide | Gel Time, Minutes | Exotherm Time, Min. | Peak Temp., °F. (°C.) |
|---|---|---|---|---|
| 1. | di(Phenoxyethyl) peroxydicarbonate | 5.45 | 5.62 | 249 (121) |
| 2. | di(4-t-Butylcyclohexyl) peroxydicarbonate | 2.46 | 3.39 | 282 (139) |
| 3. | Acetyl peroxystearyl carbonate | 3.13 | 4.05 | 299 (148) |
| 4. | APCD | 3.38 | 4.05 | 307 (153) |

TABLE VI

Hot Block Gel Tests With Polyester Resin
Resin: MR 941 (U.S.S. Chemical - orthophthalic)
Block Temperature: 180° F.
Concentrations of peroxide adjusted to 100% purity basis, 1% wt

| | Peroxide | Gel Time, Minutes | Exotherm Time, Min. | Peak Temp., °F. (°C.) |
|---|---|---|---|---|
| 1. | di(4-t-Butylcyclohexyl) peroxydicarbonate | 2.74 | 3.58 | 282 (139) |
| 2. | APCD | 3.58 | 4.20 | 301 (149) |
| 3. | BPCD | 4.28 | 5.28 | 288 (142) |
| 4. | LPCD | 4.05 | 4.96 | 262 (128) |

Aside from the employment of the novel compounds of the present invention, the practice of the instant method in curing of polyester resins is consistent with known procedures whereby the resin is heated at a curing temperature in the presence of a curing catalyst.

The unsaturated polyester resins cured by the present process comprise a mixture of a linear or only slightly branched polyester resin and a peroxide crosslinkable monomeric compound. The linear or slightly branched polyester resin is typically prepared as a condensation or reaction product of an unsaturated polybasic and a polyhydric compound; for example, the condensation product of an unsaturated dibasic acid of alpha-beta ethylenic unsaturation and a di or trihydric compound, such as a glycol. Often a saturated polybasic acid or anhydride, such as a dibasic acid, is employed with the unsaturated acid or anhydride to modify the reactivity of the unsaturated resin.

Typical examples are polyhydric alcohols, saturated polybasic acids, unsaturated polybasic acids and peroxide curable crosslinking monomers and other variations in the formulation are typical of the prior art as described in U.S. Pat. No. 4,285,877, column 6, lines 9-60, said disclosure being incorporated herein by reference.

I claim:

1. Di(acylperoxy)-bis-carbonates of the formula:

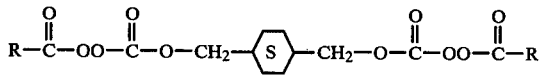

wherein each R has up to 20 carbon atoms and is alkyl or phenyl, wherein phenyl may contain alkyl, halo or alkoxy ring substituents.

2. Di(acylperoxy)-bis-carbonates in accordance with claim 1 wherein each R is selected from phenyl and alkyl of up to about 12 carbon atoms.

3. Di(acylperoxy)-bis-carbonates in accordance with claim 1 wherein each R is methyl.

4. Di(acylperoxy)-bis-carbonates in accordance with claim 1 wherein each R is hendecyl.

5. Di(acylperoxy)-bis-carbonates in accordance with claim 1 wherein each R is phenyl.

* * * * *